United States Patent [19]
Wisniewski

[11] Patent Number: 6,079,215
[45] Date of Patent: Jun. 27, 2000

[54] METHOD FOR FREEZE GRANULATION

[75] Inventor: Richard Wisniewski, San Mateo, Calif.

[73] Assignee: Integrated Biosystems, Inc., Benicia, Calif.

[21] Appl. No.: 09/003,283

[22] Filed: Jan. 6, 1998

[51] Int. Cl.[7] .................................................. F17C 11/00
[52] U.S. Cl. .................... 62/46.1; 62/64; 62/68; 62/343
[58] Field of Search .................. 62/64, 52.1, 68, 62/373, 374, 342, 343

[56] References Cited

U.S. PATENT DOCUMENTS

| | | | |
|---|---|---|---|
| 2,879,005 | 3/1959 | Jarvis | 62/64 X |
| 3,214,928 | 11/1965 | Oberdorfer | 62/64 |
| 3,393,152 | 7/1968 | Smith et al. | 252/67 |
| 3,416,977 | 12/1968 | Rein | 148/20.6 |
| 4,187,689 | 2/1980 | Selcukoglu et al. | 62/54 |
| 4,265,921 | 5/1981 | Lermuzeaux | 426/444 |
| 4,314,451 | 2/1982 | Leeds et al. | 62/68 |
| 4,476,686 | 10/1984 | Madsen et al. | 62/63 |
| 4,687,672 | 8/1987 | Vitkovsky | 426/524 |
| 4,761,962 | 8/1988 | Andersson | 62/63 |
| 4,843,840 | 7/1989 | Gibson | 62/375 |
| 4,848,094 | 7/1989 | Davis et al. | 62/64 |
| 5,135,553 | 8/1992 | Rebhan | 62/35 |
| 5,154,062 | 10/1992 | Gaumer, Jr. et al. | 62/54.1 |
| 5,205,129 | 4/1993 | Wright et al. | 62/68 |
| 5,368,105 | 11/1994 | Chaiken et al. | 169/44 |
| 5,728,417 | 3/1998 | Horn et al. | 426/231 |
| 5,732,559 | 3/1998 | Horn et al. | 62/62 |
| 5,743,097 | 4/1998 | Frank | 62/68 |

FOREIGN PATENT DOCUMENTS

| | | |
|---|---|---|
| 2041341 | 10/1992 | Canada . |
| 0 195 919 A2 | 1/1986 | European Pat. Off. .......... A23B 4/06 |
| 0 560 509 A1 | 9/1993 | European Pat. Off. . |
| 0 711 511 A2 | 5/1996 | European Pat. Off. .......... A23L 3/36 |
| 3833753A1 | 8/1989 | Germany . |
| 7-294085 | 11/1995 | Japan . |

OTHER PUBLICATIONS

Japanese Patent JP 07 294085 (Iwatani Ind. Co., Ltd.), Nov. 10, 1995 (Abstract), Database WPI, Section PQ, Week 9603, Derwent Publications Ltd., London.

Primary Examiner—Ronald Capossela
Attorney, Agent, or Firm—Wilson Sonsini Goodrich & Rosati

[57] ABSTRACT

The present invention is a system and method for freeze granulation of a medium such as a biopharmeceutical product. The medium is put into a chamber and mixed using a pair of counter rotating agitators. The agitators have angled blades or paddles on them in order to induce motion in the medium parallel to the axis of the agitator shafts. A set of liquid nitrogen and liquid carbon dioxide nozzles are attached to the chamber. The liquid nitrogen nozzles spray a mist of liquid nitrogen into the medium. The liquid carbon dioxide nozzles spray carbon dioxide snow into the chamber. The liquid nitrogen and the carbon dioxide can be sprayed into the chamber at the same time or alternately.

53 Claims, 8 Drawing Sheets

METHOD FOR FREEZE GRANULATION

FIELD OF THE INVENTION

The present invention relates to the freezing of products using liquid nitrogen and carbon dioxide snow, and in particular to the creation of frozen granules of the product using both liquid nitrogen and carbon dioxide snow.

BACKGROUND

Cryopreservation and cryoprocessing of mediums such as biopharmeceuticals and foods are important in the manufacturing, use, and sale of these products. However, in order to process many of these products, the cryopreservation or cryoprocessing must be done uniformly and in a controlled manner or the value of the product may be lost. For example, when processing cells for cryopreservation, if the cells are frozen too quickly with too high of a water content, then the cells will rupture and become unviable.

Uniformity can be achieved using small containers in which the volume of the medium in the container is small enough to allow it to be uniformly cooled. However, such small containers only allow small quantities of a product to be processed at one time, and thus are of limited commercial value. Additionally, as the size of the container is increased, the processing speed must be reduced in order to maintain uniformity in the processing.

One technique which has been used to cryoprocess foods in larger quantities is a system which mixes the product as it is frozen. Using traditional refrigerators or freezers during this process would take too long since the heat is extracted from the medium too slowly. Therefore, commercial systems have operated by spraying carbon dioxide snow on the product while it is mixed in order to rapidly cool it. Carbon dioxide snow, however, is a solid and therefore often makes less thermally conductive contact with solids in the medium and will not usually cool them quickly. This is beneficial for products which can be denatured if they are cooled too rapidly.

Liquid nitrogen is colder than carbon dioxide snow and can more quickly extract heat from a medium or product. Some commercial cryoprocessing systems have operated by spraying liquid nitrogen on the product or mixing the product with a liquid nitrogen mist. This allows for very rapid processing of a product and makes liquid nitrogen very useful in commercial cryoprocessing. Liquid nitrogen, however, may cool a product too quickly and can damage or destroy the usefulness of the product by, for example, denaturing it.

What is needed is a system and a method for cryoprocessing or cryopreservation of a medium or product which can make use of the properties of carbon dioxide snow and liquid nitrogen for cryoprocessing or cryopreservation of a medium or product without destroying its commercial utility.

SUMMARY OF INVENTION

One embodiment of the present invention is a system and method for freeze granulation of a medium such as a biopharmeceutical product. The medium is put into a chamber and mixed using a pair of counter rotating agitators. The agitators have angled blades or paddles on them in order to induce motion in the medium parallel to the axis of the agitator shafts. A set of liquid nitrogen and liquid carbon dioxide nozzles are attached to the chamber. The liquid nitrogen nozzles spray a mist of liquid nitrogen into the medium. The liquid carbon dioxide nozzles spray carbon dioxide snow into the chamber. The liquid nitrogen and the carbon dioxide can be sprayed into the chamber at the same time or alternately.

The liquid nitrogen mist and the carbon dioxide snow contact the medium when introduced into the chamber and the medium freezes. As the medium freezes the agitators mix the medium creating frozen granules of the medium.

Another embodiment of the present invention relates to a system and method for cryoprocessing or cryopresevation of a medium in a chamber. One embodiment of the invention comprises introducing a carbon dioxide snow into the chamber, introducing a liquid nitrogen mist into the chamber at the same time the carbon dioxide snow is introduced into the chamber, and mixing the medium. In other embodiments of the invention the medium is a biopharmeceutical product, a food product, or a biotechnology product.

In yet another embodiment of the invention, mixing the medium includes mixing the medium using one or more agitators. In another embodiment of the invention, the agitators include a pair of counter rotating agitators. In other embodiments of the invention mixing the medium includes moving the material which first comes into contact with the carbon dioxide snow after the carbon dioxide snow is introduced into the chamber.

In still other embodiments of the invention, mixing includes mixing at different speeds, or with different agitators. In yet other embodiments of the invention mixing includes creating a flow of the medium about a perimeter of the chamber. In other embodiments of the invention the average diameter of drops in the liquid nitrogen mist is less than 5 microns, 20 microns, 100 microns, or 1 millimeter.

In still other embodiments of the invention the rate of introduction of carbon dioxide snow and/or liquid nitrogen mist into the chamber is controlled based on a feedback loop which monitors information including the load on the agitator, the temperature of the medium, and/or the temperature of the exhaust from the chamber. In still other embodiment of the invention the medium is cooled following a predetermined protocol. In other embodiments of the invention the chamber is connected to a bioreactor chamber, a processor, a feeder, a filtration system, or a reactor.

DETAILED DESCRIPTION

Figure 1:
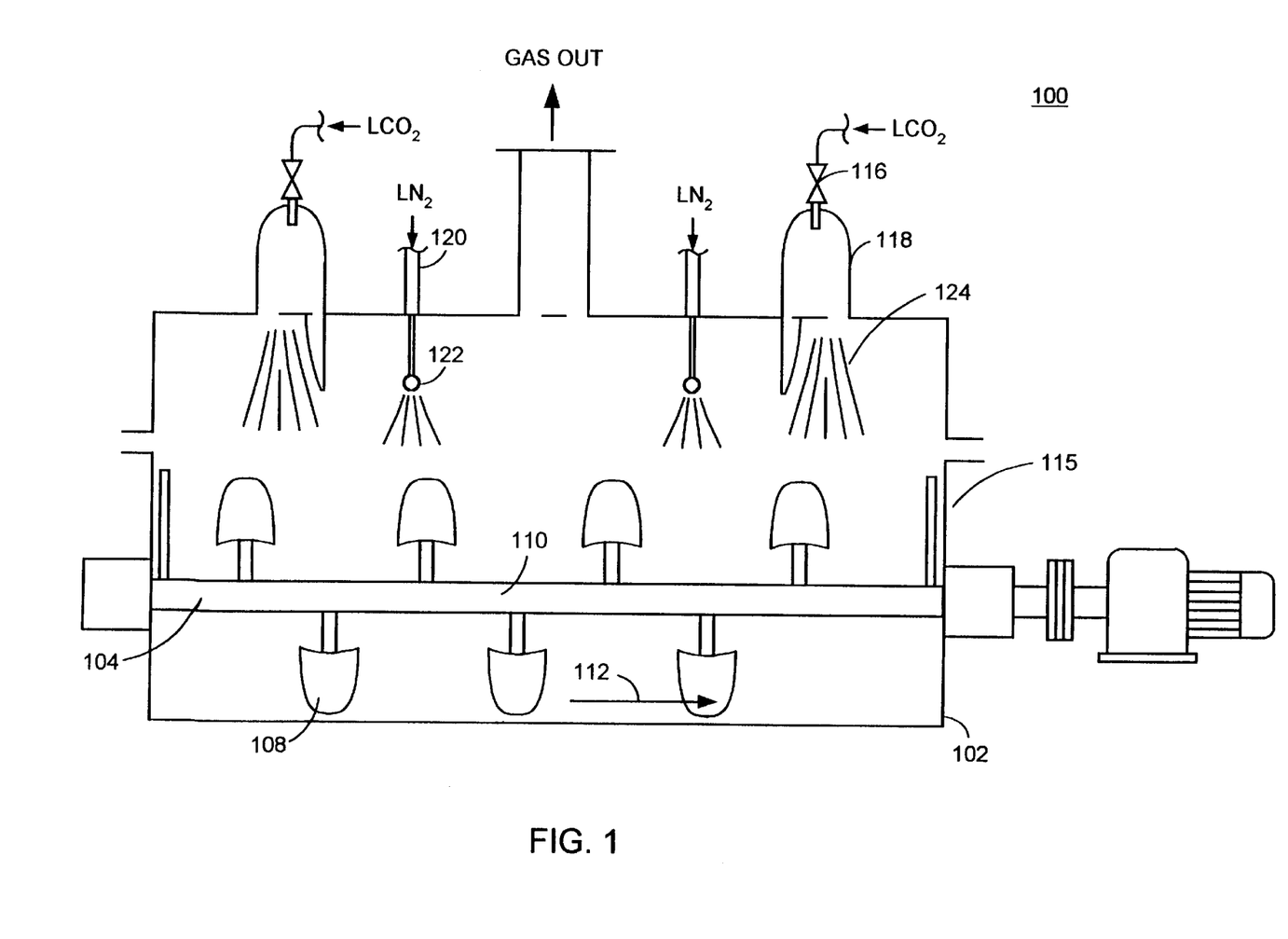
FIG. 1 depicts a side view of one embodiment of the invention showing one of the agitators and four representative paddles extending from the axis of the agitator. Additionally, liquid carbon dioxide valves, carbon dioxide snow nozzles, and liquid nitrogen nozzles are depicted.
Figure 2:
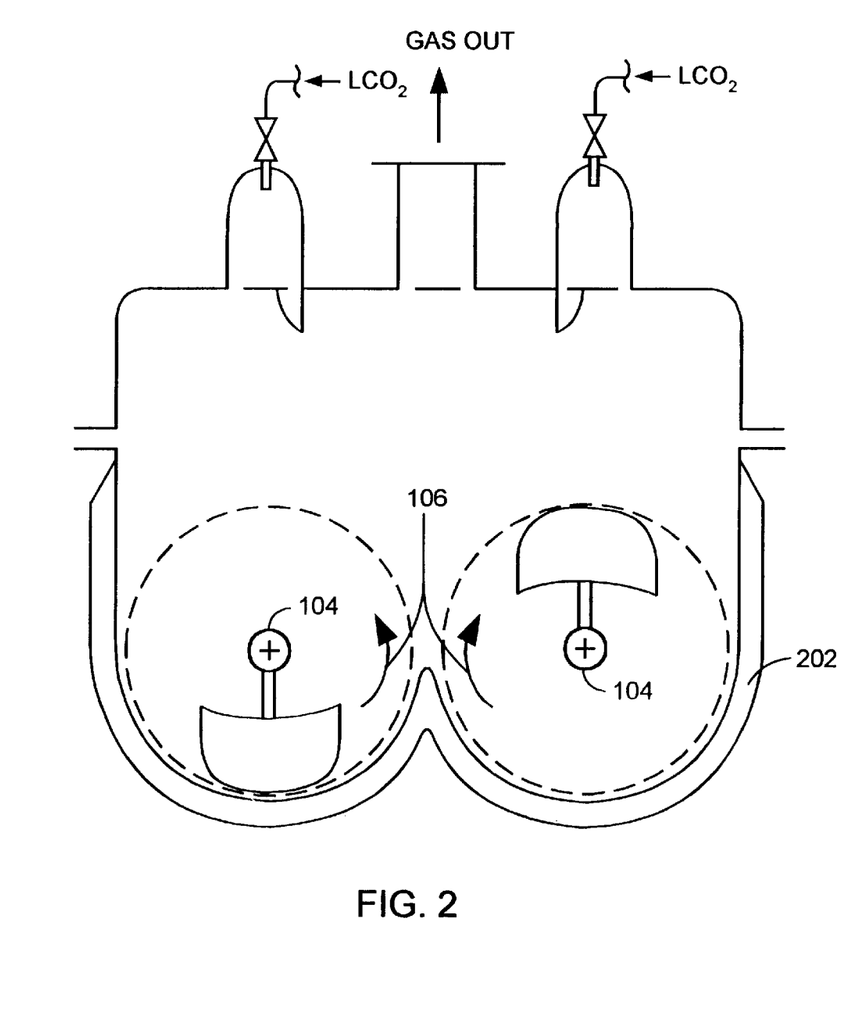
FIG. 2 is a front view of an embodiment of the invention showing a pair of counter rotating agitators and an optional heating jacket.

FIGS. 1 and 2 depict a side view and a front view, respectively, of one embodiment of the present invention. FIG. 1 shows granulating freezer system 100. Granulating freezer system 100 includes chamber 102. Chamber 102 can be of any shape or configuration and is depicted as rectangular for illustrative purposes only. Chamber 102 should be made of a material which can withstand prolonged contact with the medium to be treated or frozen in the chamber.

Inside chamber 102 is a pair of counter rotating agitators 104. In the side view of FIG. 1, only one of the agitators is visible. FIG. 2 shows a front view in which the pair of counter rotating agitators 104 are shown rotating towards each other as depicted by arrows 106. Each of the agitators includes one or more paddles 108. Paddles 108 can be in any shape or form which will cause movement of the medium. For example paddles 108 can be of any desired cross section and need not all be the same shape, the same size, or uniformly distributed along the axis of the agitator. Additionally, paddles 108 can be one or more continuous curves such as a cork screw shape around shaft 110 of agitator 104.

Figure 3:
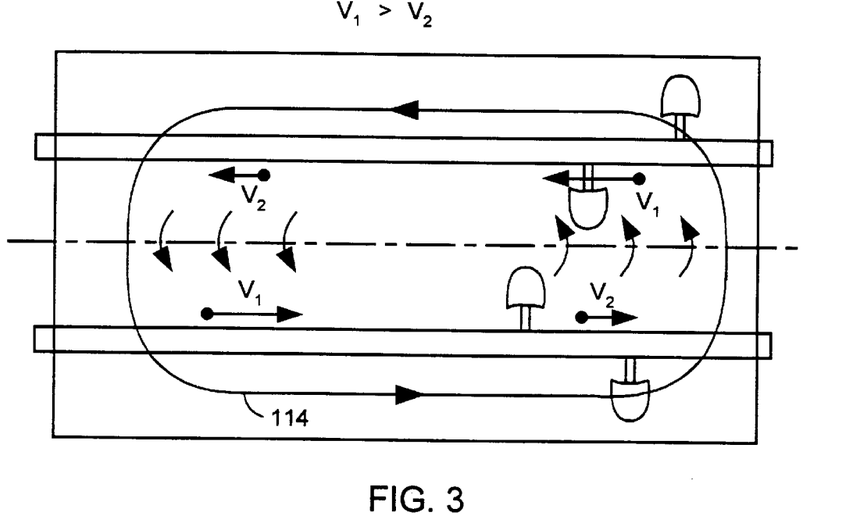
FIG. 3 is a top view of an embodiment of the invention showing a global circulation pattern induced in the medium by the angling of the paddles on the agitators.

Paddles 108 mix the medium so that it is uniformly cooled. Paddles 108 create movement of the medium in the direction of arrows 106 in FIG. 2. Additionally, in another embodiment of the invention, paddles 108 are angled so that circulation of the medium is created in the direction of arrow 112 in FIG. 1. FIG. 3 shows a top view of chamber 102. The angled paddles create circulation of the medium about a perimeter of chamber 102 as depicted by arrow 114. This global circulation helps ensure uniformity of the medium throughout chamber 108.

Figure 4A:
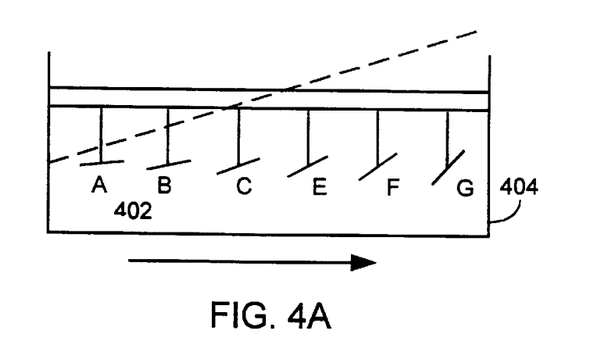
FIG. 4A depicts the angling of the paddles on an agitator to induce flow of ht medium in a direction along the axis of the agitator. Additionally, the angling of the paddles induces an increase in the level of ht medium in the direction of flow of the medium.

In one embodiment of the invention, the angle of the paddles is varied as a function of the distance of the paddle from an end of the chamber. As depicted in FIG. 4A, paddles 402A through 402G are increasingly angled to create a faster flow and a higher level of the medium at end of chamber 404. The paddles for the agitator on the other side of the chamber are angled to create a faster flow and higher level of the medium in the opposite direction.

Figure 4B:
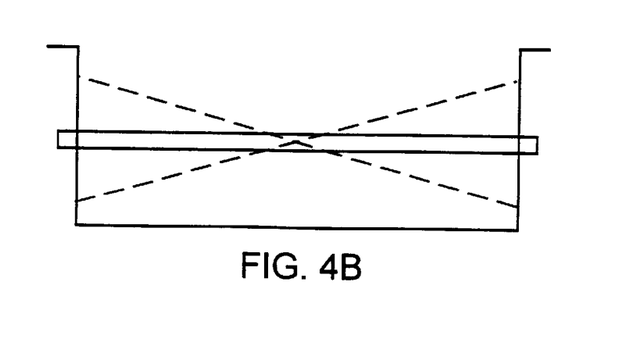
FIG. 4B depicts the level of the medium induced on both sides of the chamber through the action of both agitators.

This is depicted in FIG. 4B. The buildup of material at alternate ends of the chamber aids the creation of a circulation pattern like the one indicated by arrow 114 in FIG. 3.

In another embodiment of the invention not depicted in the figures, the paddles are angled so that two independent circulation patterns are created instead of the one shown in FIG. 3. In other embodiments multiple circulation patterns can be created. Any circulation pattern which will help to mix the contents of the chamber can be used.

Figure 5:
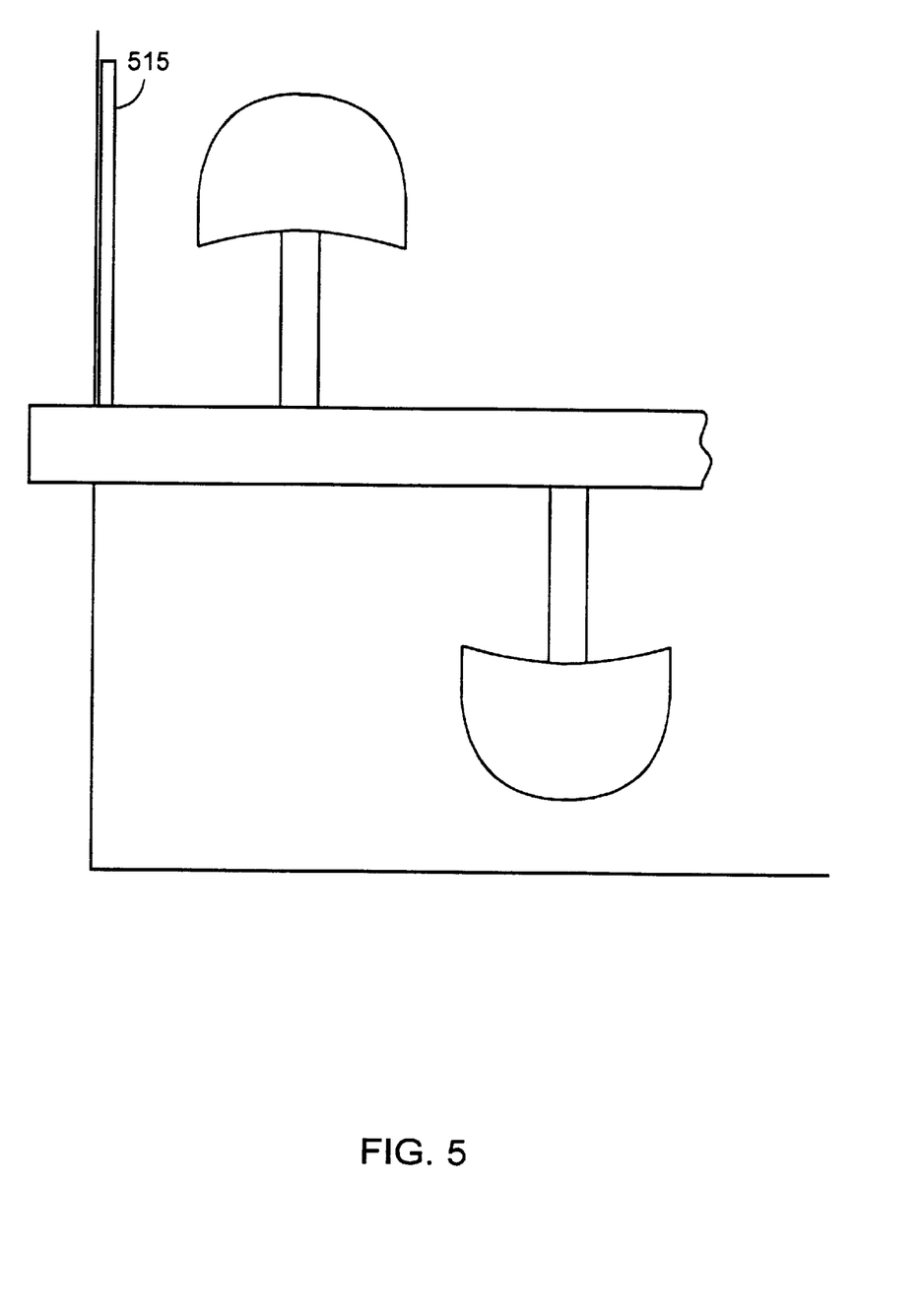
FIG. 5 depicts a detailed sketch of an embodiment of the invention showing a scrapper blade.

In the embodiment of the invention depicted in FIG. 1, optional scrapper blade 115 is used to prevent a buildup of the medium at the ends of chamber 102. FIG. 5 shows a detail sketch of a scrapper blade 515. Scrapper blade 515 can be configured so that it touches the end of the chamber or so that there is a gap between the scrapper blade and the end of the chamber. The gap can be 1 millimeter, one-sixteenth of an inch, one eighth of an inch, one fourth of an inch, one half of an inch, or larger than one half of an inch.

FIG. 2 depicts an embodiment of the invention in which optional heating layer 202 covers a portion of chamber 102. In this embodiment of the invention, a portion of the exterior of chamber 102 is insulated or slightly heated to generate a thin liquid film of the medium along the inner surface of chamber 102. Heating layer 202 can be maintained at a temperature just above the freezing point of the medium in the container so that even when the medium is becoming viscous or forming solid granules, there is a liquid layer along the inner walls of chamber 102. The liquid layer can help prevent the medium from sticking to the walls or piling up along a portion of chamber 102. Additionally, the liquid film can act as a lubricating layer, reducing the resistance of the medium on the agitators. The heating of heating layer 202 can be achieved using any conventional heat transfer mechanism including but not limited to water or other fluids such as silicon or oil, electric heaters, or infrared radiation.

In FIG. 1 liquid carbon dioxide is input into chamber 102 through valves 116 which are connected to nozzles 118. When the liquid carbon dioxide at high pressure passes through valve 116 and into nozzle 118, the pressure drops and the liquid carbon dioxide turns into solid carbon dioxide snow. The particles of carbon dioxide snow fall onto the medium and are then mixed in by agitators 104. Liquid nitrogen mist is input into chamber 102 through valves 120 which are connected to nozzles 122. The liquid nitrogen mist is deposited on the medium and mixed in by agitators 104.

In one aspect of the invention, paddles 108 extend above the surface of the medium in chamber 102 during some portion of their rotation cycle. When paddles 108 extend above the surface, they contact material on the surface, including carbon dioxide snow which may have accumulated on the surface. The surface layer, including the carbon dioxide snow is forced down into the medium by paddles 108. In other embodiments of invention, the paddles extend above the surface of the medium by less than 1 inch, less than 2 inches, more than 2 inches, 5%, 20%, or 95% of the diameter of circle made by the tip of rotating paddles 108.

When the present invention is used to cool or freeze the medium, the size of the liquid nitrogen drops used must be controlled. Liquid nitrogen is typically at a temperature much lower than that of solid carbon dioxide. The extreme cold of the liquid nitrogen mist drops, when they come in contact with the medium, may cause damage to the medium. For example, if the medium is a biopharmeceutical product it can be damaged if it is frozen while containing too much excess water. Liquid nitrogen may cause granules of the medium to freeze too rapidly without allowing sufficient time for excess water to be released from the product. As a result, frozen water in the granule may cause damage to the biopharmeceutical product.

In one embodiment of the invention the liquid nitrogen nozzle is configured to produce liquid nitrogen drops at or below a specified average size. Controlling the size of the drops and the rate at which the drops are input into the chamber allows for control of the cooling rate of the medium. In other aspects of the invention the liquid nitrogen nozzle is configured to produce drops with an average diameter of less than 5 microns, about 5 microns, less than 20 microns, about 20 microns, less than 100 microns, about 100 microns, less than 1 millimeter, or about 1 millimeter.

In the embodiment of the invention depicted in FIG. 1, chamber 102 includes baffle 124. Baffle 124 is placed in chamber 102 to deflect carbon dioxide snow particle. Baffle 124 may be positioned to ensure a directed or uniform deposition of carbon dioxide snow within chamber 102. Additionally, baffles 124 can be positioned to prevent carbon dioxide snow particles from being withdrawn from chamber 102 through gas exhaust 126 before the carbon dioxide snow particles have contacted the medium in the chamber. Gas exhaust 126 removes excess gas from chamber 102 to regulate the pressure inside chamber 102. Without baffles 124, a current set up by exhaust 126 would remove some of the carbon dioxide snow from chamber 102 before it contacted the surface of the medium. This would reduce the effectiveness of freeze granulation system 100.

In another embodiment of the invention, the rate at which carbon dioxide snow, and liquid nitrogen mist are introduced into the chamber is controlled by a computer. Either or both of these rates can be computer controlled along with the size of the drops in the liquid nitrogen mist, the speed of the agitators, the angles of the paddles, and the rate of mixing of the medium. Any or all of these parameters can be computer controlled based on a feedback loop which monitors variables in the granulation processing. Parameters which can be used by the computer to feedback on, include but are not limited to, the temperature of the medium, the temperature uniformity of the medium, temperature gradients in the medium, the temperature of the chamber, the temperature of exhaust gases, ratios or differences of any measured temperatures, the load on the agitators, the power consumption of the agitators, and/or the speed of the agitators.

Figure 6A:
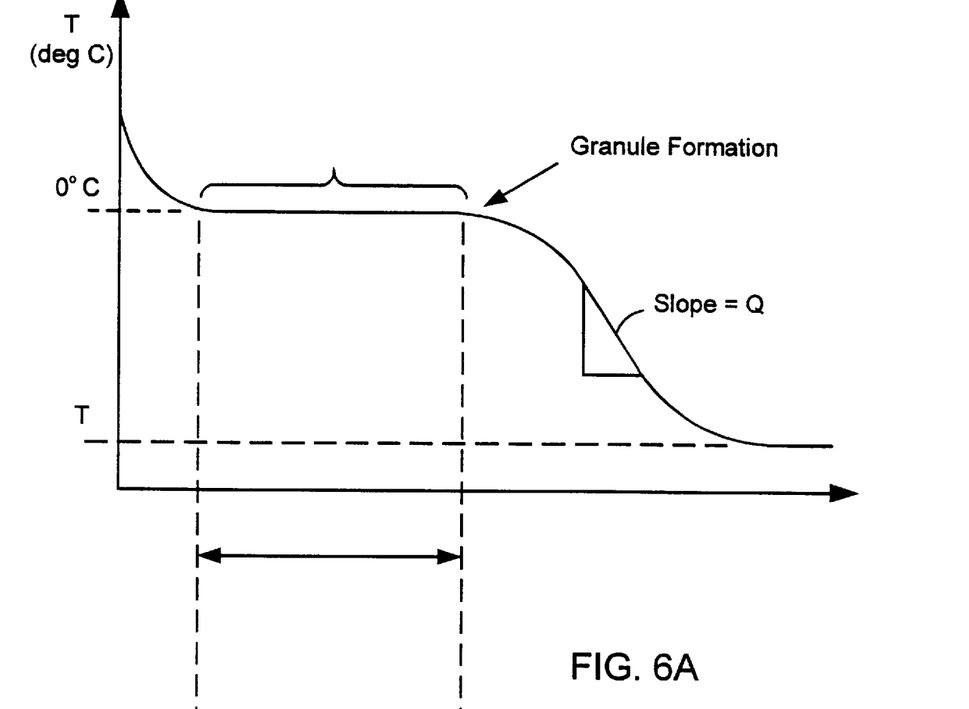
FIG. 6A is a graph showing one possible cooling protocol for an embodiment of the invention.

In another embodiment of the invention, parameters, including those listed above can be controlled over time to achieve desired processing protocols. As depicted in the graphs in FIG. 6, the temperature of the medium over time can be controlled as desired to achieve particular processing characteristics. Graph 6A depicts a temperature versus time profile in which a liquid is cooled to 0 degrees Celsius and held at that temperature for a specified period of time. At the end of the hold period, the medium is cooled at a rate of Q degrees per second until temperature T is reached. This protocol may be usefull in freeze granulating biopharmeceutical products so that excess water can be withdrawn from the product during the temperature plateau at 0 degrees Celsius.

Figure 6B:
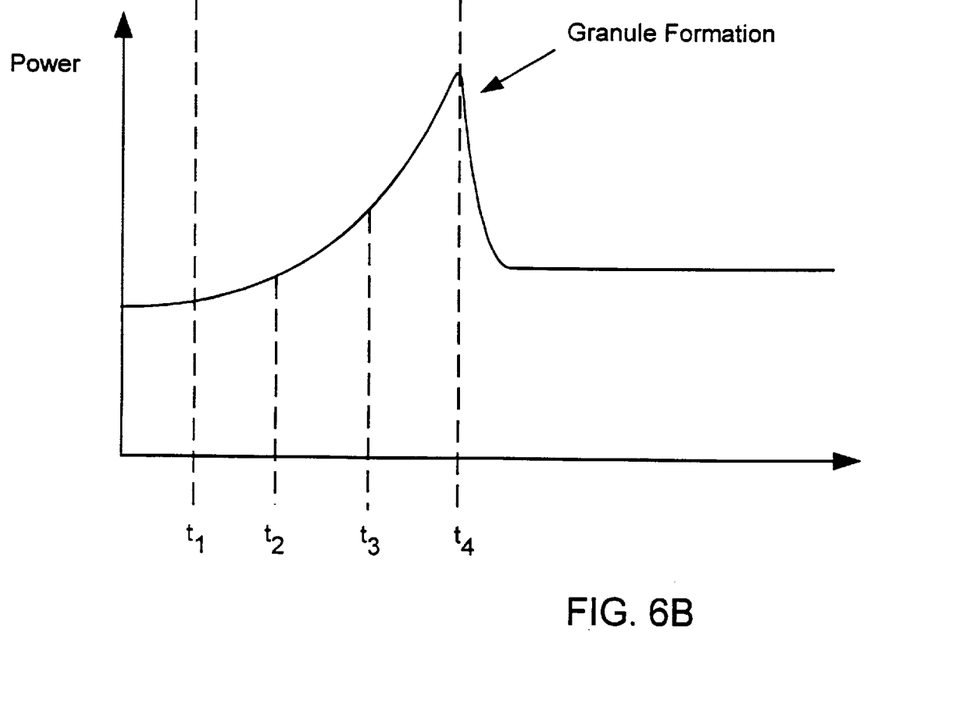
FIG. 6B is a graph showing power consumption for the agitator motors at constant agitation speed versus time for a particular medium as it is cooled following the protocol depicted in graph 6A.

Graph 6B depicts power consumption for the agitator motors as a function of time for the case in which the medium is a suspension of cells. When the medium is cooled to 0 degrees Celsius it is initially a liquid. As the medium is held at 0 degrees Celsius, water is removed from the cells and ice crystals form in the slurry surrounding the cells increasing the viscosity of the medium. After the medium has been held at 0 degrees Celsius for a time t1 the medium becomes more viscous and creates more resistance for the agitators for a constant agitation speed. This results in a slight rise in the power requirements for the agitators. After a time t2 the medium achieves a slightly higher viscosity and the power requirements for the agitators increase slightly more. Finally, at time t4 the viscosity peaks as frozen granules are formed. At this point, the feedback system can begin to decrease the temperature below 0 degrees Celsius since the medium has solidified into granules. This is depicted in FIG. 6A by the downward slope of the temperature versus time curve. FIG. 6B is an example of a parameter, power consumption, that may be used by a computer controlled feedback system to achieve a desired protocol. FIG. 6B shows how once granule formation has been completed, the power consumption of the agitators falls dramatically. Other parameters can be used by the feedback system without departing from the present invention.

In general, as the consistency of a medium changes from a liquid to a viscous mass just prior to breaking up into granules, the power required to agitate or mix the medium increases. The peak power requirements for the agitators can be reduced through the use of a heating jacket such as the one depicted in FIG. 2. The thin layer of liquid created by the heating jacket reduces the viscosity of the medium near the walls of the container, reducing the power needed to mix the medium. The jacket can be heated just prior to the peak power points or continuously throughout the cooling process. Once the medium breaks up into granules, its viscosity decreases rapidly and the power required to mix it is reduced dramatically.

Figure 7:
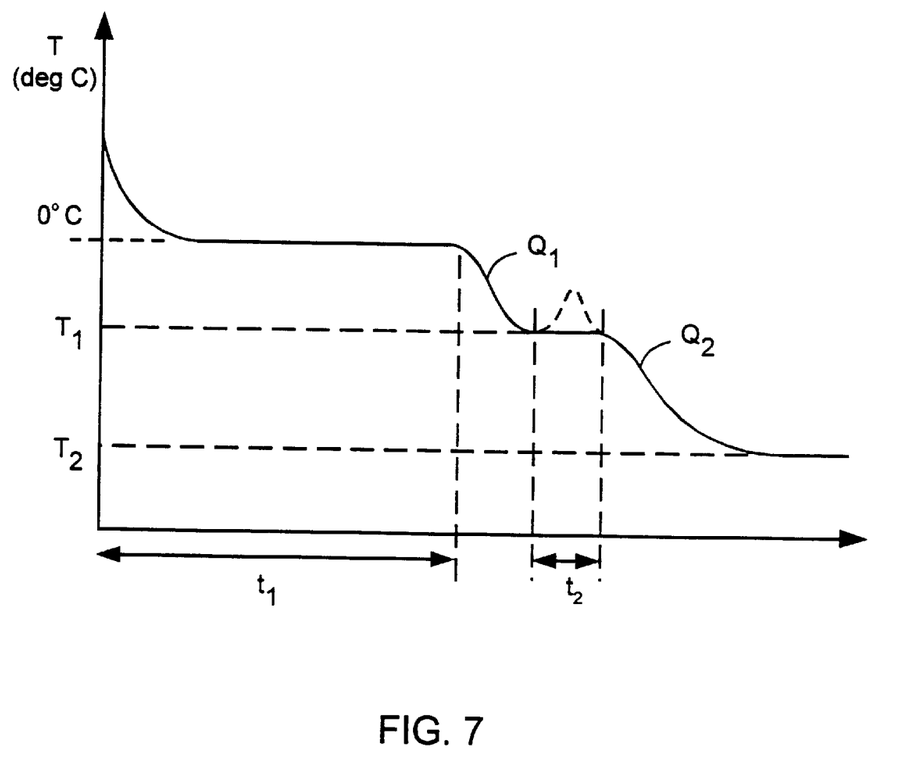
FIG. 7 is a graph depicting another protocol in which there are two different cooling rates Q1 and Q2.

FIG. 7 shows another example of a protocol of temperature versus time which can be achieved using the present invention. The medium is cooled to 0 degrees Celsius and held there for a time t1. The medium is then cooled at a rate of Q1 degrees per second to a temperature T1 and held there for t2 seconds. The medium is then cooled at a rate of Q2 degrees per second to a temperature of T2 and held there until needed. Additionally, processing is possible using the present invention. As depicted by the dotted curve at the T1 temperature plateau, the temperature versus time profile can be varied in a non-linear fashion if desired.

Figure 8:
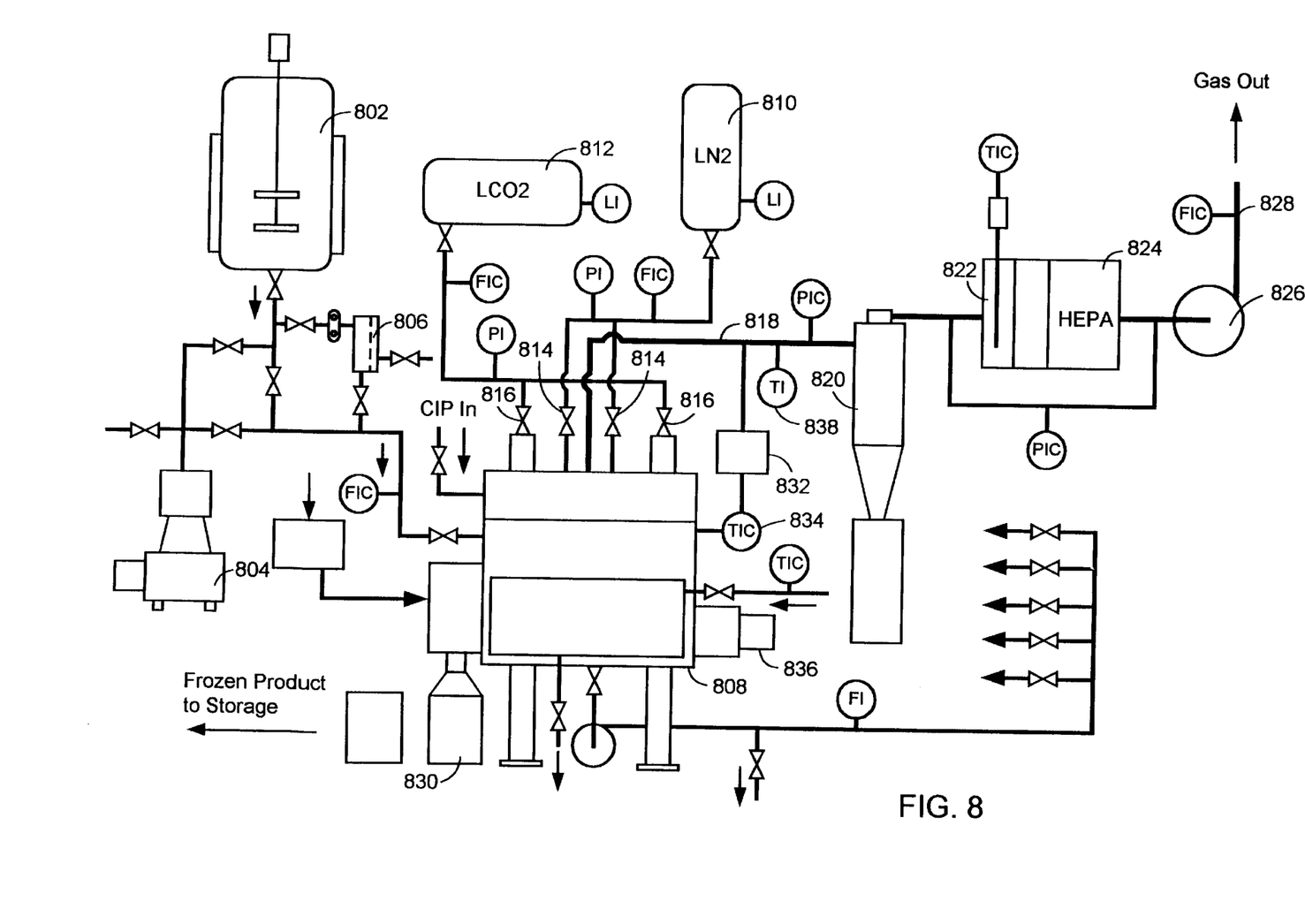
FIG. 8 shows one embodiment of a system containing many subcomponents for processing a medium using a freeze granulator

FIG. 8 depicts an embodiment of a freeze granulator system including many processing subcomponents. In this embodiment of the invention, bioreactor chamber 802 is coupled to centrifuge 804, filtration system 806, and granulation chamber 808 through a system of pipes and valves. Bioreactor chamber 802, centrifuge 804 and filtration system 806 allow a medium, such as a biopharmeceutical product, or a protein to be processed prior to freeze granulation in granulation chamber 808. Other processing systems can be attached to granulation chamber 808 without departing from the present invention, including but not limited to food processing equipment, cosmetics processing equipment, or biotechnology processing equipment.

Freeze granulator 808 is coupled to liquid nitrogen storage container 810 and liquid carbon dioxide storage container 812. Liquid nitrogen mist and carbon dioxide snow are input into granulation chamber 808 through values 814 and 816 respectively. In other embodiments of the invention, storage containers 810 and 812 include pressurizing cells which maintain the pressure inside containers 810 and 812 above a minimum level. This may be especially important for liquid carbon dioxide container 812 because liquid carbon dioxide may solidify if not kept at high enough pressure.

Exhaust gases are vented from freeze granulator 808 through exhaust line 818. Exhaust line 818 is connected to the top of freeze granulator 808, and to particle separator 820. Particle separator 820 is connected to heater 822 and gas filters 824. Particle separator 820 removes large particles from the exhaust gas before the gas gets to filter 824. Heater 822 is used to warm the exhaust gas to prevent solid particles such as carbon dioxide snow particles from clogging filter 824. Exhaust blower 826 pulls the exhaust gas through the exhaust line and pushes it out through gas out line 828. In other embodiments of the invention filter sets can be used instead of filter 824. one filter at a time from the set can be automatically switched into position which the other filters in the set are cleaned. This allows a clean filter to continuously be positioned in the exhaust line. It is noted that other embodiments of the invention do not include particle separator 820, heater 822, gas filters 824, exhaust blower 826 and/or gas out line 828.

After the medium has been freeze granulated, it is emptied out of freeze granulator 808 through output 830 and can be stored or transferred to another site or container. In one embodiment of the invention, filter and blower 832 is used when the medium is emptied from freeze granulator 808 in order to maintain a positive pressure inside freeze granulator 808.

In an embodiment of the invention not depicted in FIG. 9, the seal for the agitator shafts extending into freeze granulator 808 are kept at a pressure higher than that in freeze granulator 808 using, for example, filtered dry gas. The increased pressure in the seals prevents the contents of freeze granulator 808 from coming into contact with the seal surfaces. Additionally, pressurizing the seals can be used to detect possible seal failures. If the seals are pressurized and the seals fail, leaking into the chamber, then the pressure in the chamber will increase. Additionally, pressure sensors connected to the seals will detect a drop in pressure if the seals fail.

In another embodiment freeze granulator 808 is coupled to a cleaning solution inlet. When it is desired to clean freeze granulator 808, it is partially filled with cleaning solution, and the agitators are turned on. The agitators can be run at high speed to ensure a thorough cleaning of freeze granulator 808, and the cleaning fluid may be recirculated through the seal chambers in order to clean them. A heating layer around a portion of freeze granulator 808, if present, may be used during cleaning to heat the cleaning fluid, and temperature monitors can be used to monitor and control the cleaning process.

In another embodiment of the invention, steam or hydrogen peroxide vapor may be used to sterilize the system. A heating layer, if present, may be used to heat the freeze granulator and aid in the steam or hydrogen peroxide vapor cleaning.

Referring to FIG. 8, computer controller 832 couples temperature indicator and controller 834, agitator motor monitor and controller 836, liquid nitrogen valves 814, liquid carbon dioxide valves 816, and exhaust gas line temperature and pressure monitor 838 in a closed feedback system. The temperature of the medium in the freeze granulator 808 and the exhaust gas are measured using sensors 834 and 838 respectively. The load and speed of the agitators is measured using sensor 836. These measured values are used to feedback through computer controller 832 in order to adjust the flow rate of liquid nitrogen and carbon dioxide snow into the freeze granulator 808 using valves 814 and 816 respectively.

Using this feedback loop a predetermined protocol can be achieved. For example, the medium in freeze granulator 808 can be maintained at a constant temperature for a specified period of time by measuring the temperature of the medium using sensor 834 and maintaining the temperature at a constant level by varying the flow of liquid nitrogen into freeze granulator 808 through valve 814 and/or varying the flow of carbon dioxide snow into freeze granulator 808 using valve 816. In order to achieve this result, a control signal is generated by computer controller 832 which is proportional to the difference between the actual temperature measured by sensor 834 and a desired value. The control signal is used to adjust the actuators connected to valves 814 and 816 in order to allow more or less liquid nitrogen or carbon dioxide snow into freeze granulator 808. It is noted that more than one temperature sensor can be used without departing from the present invention. Additionally, computer controller 832 could alternatively be implemented using any analog or digital control system.

Figure 9A:
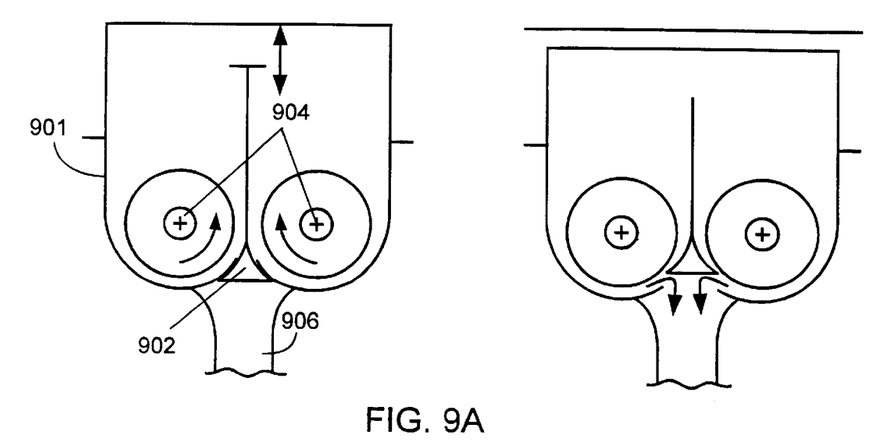
FIG. 9 depicts 3 configurations which can be used to allow a freeze granulator chamber to be emptied.
Figure 9B:
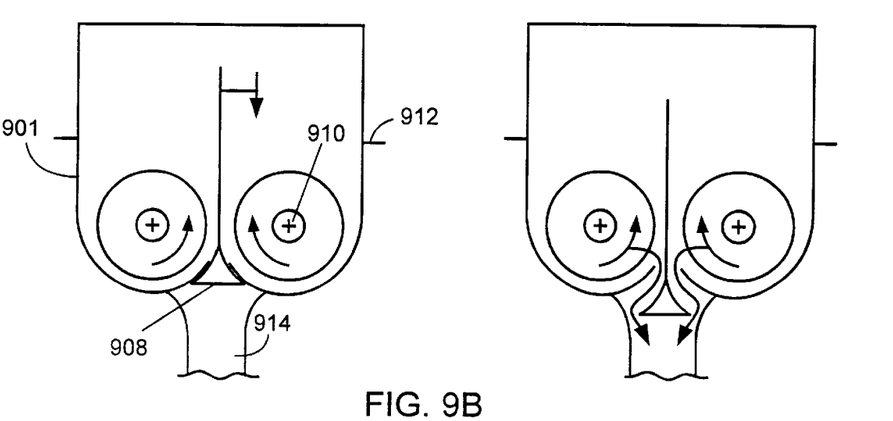
Figure 9C:
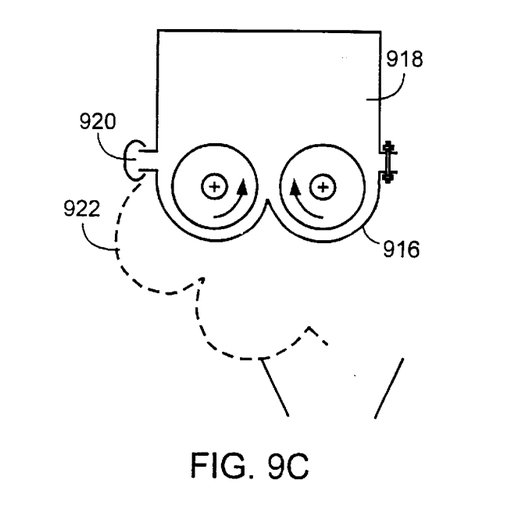

FIG. 9 shows three alternative embodiments for freeze granulator 901 which can be used to discharge the medium. In FIG. 9A central plug 902 between agitators 904 is lifted opening up chute 906 to allow the medium out of freeze granulator 901. In FIG. 9B central plug 908 between agitators 910 drops down to allow the medium to exit freeze granulator 912 through chute 914. In FIG. 9C, bottom section 916 of freeze granulator 918 is hinged at hinge 920 and can be opened to position 922 to empty the medium from freeze granulator 918.

What is claimed is:

1. A method for cryopreservation of a medium in a chamber, comprising:

introducing a carbon dioxide snow into the chamber;

introducing a liquid nitrogen mist into the chamber after the introduction of carbon dioxide snow into the chamber has stopped; and mixing the medium product until it is cryopreserved.

2. The method of claim 1, wherein:

the medium is a biopharmeceutical product.

3. The system of claim 1, wherein:

the medium is a food product.

4. The system of claim 1, wherein:

the medium is a biotechnology product.

5. The method of claim 1, wherein:

mixing the medium includes mixing the medium with counter rotating agitators.

6. The method of claim 5, wherein:

the agitators includes a paddle.

7. The method of claim 6, wherein:

a mixing surface of the paddle is at angle greater than 90 degrees to the direction of motion of the paddle.

8. The method of claim 6, wherein:

a mixing surface of the paddle is at about an angle of 90 degrees to the direction of motion of the paddle.

9. The method of claim 5, wherein:

the agitators includes a plurality of paddles.

10. The method of claim 1, wherein:

mixing includes moving the material which first comes into contact with the carbon dioxide snow after the introducing of the carbon dioxide snow into the chamber.

11. The method of claim 1, wherein:

mixing includes varying the rate of mixing.

12. The method of claim 1, wherein:

mixing includes varying the speed of the agitators.

13. The method of claim 1, wherein:

mixing includes operating the agitators at different speeds.

14. The method of claim 1, wherein:

mixing the medium includes creating a flow of the medium about a perimeter of the chamber.

15. The method of claim 14, wherein:

mixing the medium includes creating a flow of the medium transverse to the flow of the medium about the perimeter of the chamber.

16. The method of claim 14, wherein:

the perimeter of the chamber includes a segment parallel to the axis of rotation of at least one of the agitators.

17. The method of claim 1, wherein:
the chamber includes a structure to allow for thermally induced changes in size of the chamber.

18. The method of claim 17, wherein:
the structure includes an expansion bearing attached to at least one of the agitators.

19. The method of claim 1, comprising:
a pressurized carbon dioxide container coupled to the chamber.

20. The method of claim 19, comprising:
a system for maintaining a predetermined minimum pressure in the pressurized carbon dioxide container.

21. The method of claim 1, wherein:
an average diameter of drops in the liquid nitrogen mist is about 5 microns.

22. The method of claim 1, wherein: an average diameter of drops in the liquid nitrogen mist is less than 5 microns.

23. The method of claim 1, wherein:
an average diameter of drops in the liquid nitrogen mist is about 20 microns.

24. The method of claim 1, wherein:
an average diameter of drops in the liquid nitrogen mist is less than 20 microns.

25. The method of claim 1, wherein:
an average diameter of drops in the liquid nitrogen mist is about 100 microns.

26. The method of claim 1, wherein:
an average diameter of drops in the liquid nitrogen mist is less than 100 microns.

27. The method of claim 1, wherein:
an average diameter of drops in the liquid nitrogen mist is about 1 millimeter.

28. The method of claim 1, wherein:
an average diameter of drops in the liquid nitrogen mist is less than 1 millimeter.

29. The method of claim 1, wherein:
the rate of introducing of carbon dioxide snow into the chamber is controlled based on a feedback loop which monitors information including a temperature of the medium.

30. The method of claim 1, wherein:
mixing includes mixing using an agitator; and
a rate of introducing of carbon dioxide snow into the chamber is controlled based on a feedback loop which monitors information including a load on the agitator.

31. The method of claim 1, wherein:
mixing includes mixing using an agitator; and
a rate of introducing of carbon dioxide snow into the chamber is controlled based on a feedback loop which monitors information including a temperature of the medium and a load the agitator.

32. The method of claim 1, wherein:
a rate of introducing of liquid nitrogen mist into the chamber is controlled based on a feedback loop which monitors information including a temperature of the medium.

33. The method of claim 32, wherein:
the temperature of the medium is measured at more than one location.

34. The method of claim 1, wherein:
mixing includes mixing using an agitator; and
a rate of introducing of liquid nitrogen mist into the chamber is controlled based on a feedback loop which monitors information including a load on the agitator.

35. The method of claim 1, wherein:
mixing includes mixing using an agitator; and
a rate of introducing of liquid nitrogen mist into the chamber is controlled based on a feedback loop which monitors information including a temperature of the medium and a load on agitator.

36. The method of claim 1, wherein:
mixing includes mixing using an agitator; and
the carbon dioxide snow is input into the chamber at a rate which is controlled based on a feedback loop which monitors information including a temperature of the medium and a load on the agitator.

37. The method of claim 1, wherein:
a rate of introducing of liquid nitrogen mist into the chamber is controlled by a computer controlled feedback loop.

38. The method of claim 1, wherein:
the carbon dioxide snow is input into the chamber at a rate which is controlled by a computer controlled feedback loop.

39. The method of claim 1, wherein:
a rate of introducing of carbon dioxide snow and liquid nitrogen mist into the chamber is controlled by a computer controlled feedback loop.

40. The method of claim 1, comprising:
a computer controlled feedback loop controlling the mixing of the medium in the chamber.

41. The method of claim 1, comprising:
a computer controlled feedback loop controlling a rate of the mixing of the medium in the chamber, a rate of introducing of carbon dioxide snow, and a rate of introducing of liquid nitrogen mist into the chamber.

42. The method of claim 41, wherein:
the computer controlled feedback loop includes measuring a temperature of the medium in the chamber and a load on at least one of the agitators.

43. The method of claim 42, wherein:
a temperature of the medium in the chamber includes measuring the temperature at more than one location.

44. The method of claim 1, comprising:
cooling the medium at a predetermined rate.

45. The method of claim 1, comprising:
cooling the medium following a predetermined protocol.

46. The method of claim 45, wherein:
the predetermined protocol includes varying a rate of cooling the medium.

47. The system of claim 45, wherein:
the predetermined protocol includes varying a rate of the mixing.

48. The method of claim 1, wherein:
the chamber is connected to a bioreactor chamber.

49. The method of claim 48, comprising:
a filtration system connected to the bioreactor chamber and to the chamber.

50. The method of claim 1, comprising:
a reactor chamber connected to the chamber.

51. The method of claim 1, comprising:
a processor connected to the chamber.

52. The method of claim 1, comprising:
a feeder connected to the chamber.

53. The method of claim 1, wherein:
introducing the carbon dioxide snow into the chamber includes using a valve which is capable of shutting off a flow of the carbon dioxide snow into the chamber and then restarting the flow of carbon dioxide snow into the chamber.

* * * * *